(12) United States Patent
Edgett et al.

(10) Patent No.: US 8,323,256 B2
(45) Date of Patent: Dec. 4, 2012

(54) TAMPON REMOVAL DEVICE

(75) Inventors: Keith Edgett, Middletown, DE (US); Patrick Gorham, Wyoming, DE (US)

(73) Assignee: Playtex Products Inc., Westport, CT (US)

( * ) Notice: Subject to any disclaimer, the term of this patent is extended or adjusted under 35 U.S.C. 154(b) by 0 days.

(21) Appl. No.: 11/895,857

(22) Filed: Aug. 28, 2007

(65) Prior Publication Data

US 2008/0058751 A1 Mar. 6, 2008

Related U.S. Application Data

(60) Provisional application No. 60/840,886, filed on Aug. 29, 2006.

(51) Int. Cl.
*A61F 13/20* (2006.01)

(52) U.S. Cl. .................... 604/385.18; 604/904; 604/359

(58) Field of Classification Search .............. 604/385.18, 604/904, 359
See application file for complete search history.

(56) References Cited

U.S. PATENT DOCUMENTS

| | | | |
|---|---|---|---|
| 2,024,218 A | | 12/1935 | Haas |
| 2,146,985 A | | 2/1939 | Rabell |
| 2,519,912 A | | 8/1950 | Laun |
| 2,662,116 A | | 12/1953 | Potier |
| 3,037,506 A | | 6/1962 | Penksa |
| 3,102,541 A | | 9/1963 | Adams |
| 3,204,635 A | | 9/1965 | Voss et al. |
| 3,452,752 A | | 7/1969 | De Crescenzo |
| 3,520,302 A | | 7/1970 | Jones |
| 3,589,364 A | | 6/1971 | Dean et al. |
| 3,625,787 A | | 12/1971 | Radl et al. |
| 3,674,030 A | * | 7/1972 | Jones et al. .................... 604/369 |
| 3,756,238 A | | 9/1973 | Hanke |
| 3,794,024 A | | 2/1974 | Kokx et al. |
| 3,796,219 A | | 3/1974 | Hanke |
| 3,815,600 A | * | 6/1974 | Groves .......................... 604/286 |
| 3,830,237 A | * | 8/1974 | Bernardin et al. ............. 604/359 |
| 3,857,395 A | | 12/1974 | Johnson et al. |
| 3,902,493 A | * | 9/1975 | Baier et al. .................... 604/286 |
| RE28,674 E | | 1/1976 | Guyette |
| 3,948,257 A | | 4/1976 | Bossak |
| 3,999,549 A | | 12/1976 | Poncy et al. |
| 4,230,686 A | | 10/1980 | Schopflin et al. |
| 4,317,454 A | | 3/1982 | Bucalo |
| 4,332,251 A | | 6/1982 | Thompson |
| 4,563,485 A | * | 1/1986 | Fox et al. ....................... 523/113 |
| 4,690,671 A | * | 9/1987 | Coleman et al. ................ 604/12 |
| 4,743,237 A | | 5/1988 | Sweere |
| 4,755,166 A | | 7/1988 | Olmstead |
| 5,203,767 A | | 4/1993 | Cloyd |
| 5,429,628 A | | 7/1995 | Trinh et al. |
| 5,458,589 A | | 10/1995 | Comin-DuMong |
| 5,478,335 A | | 12/1995 | Colbert |
| 5,533,990 A | | 7/1996 | Yeo |
| 5,618,281 A | | 4/1997 | Betrabet et al. |
| 5,647,863 A | | 7/1997 | Hammons et al. |
| 5,649,914 A | | 7/1997 | Glaug et al. |
| 5,681,298 A | | 10/1997 | Brunner et al. |
| 5,702,376 A | | 12/1997 | Glaug et al. |
| 5,728,125 A | | 3/1998 | Salinas |
| 5,744,151 A | * | 4/1998 | Capelli ........................... 424/405 |
| 5,769,813 A | | 6/1998 | Peller et al. |
| 5,797,892 A | | 8/1998 | Glaug et al. |
| 5,840,055 A | | 11/1998 | Sgro |
| 5,891,126 A | | 4/1999 | Osborn, III et al. |
| 6,264,640 B1 | * | 7/2001 | Sutton ...................... 604/385.18 |
| 6,415,484 B1 | * | 7/2002 | Moser .............................. 28/118 |
| 6,495,097 B1 | | 12/2002 | Streit et al. |
| 6,703,536 B2 | * | 3/2004 | Roe et al. ........................ 604/360 |
| 2002/0010447 A1 | | 1/2002 | Williams et al. |
| 2004/0131820 A1 | * | 7/2004 | Turner et al. ...................... 428/92 |
| 2005/0203473 A1 | | 9/2005 | Pesce et al. |
| 2006/0008514 A1 | | 1/2006 | Koenig et al. |

FOREIGN PATENT DOCUMENTS

| | | |
|---|---|---|
| EP | 1 140 009 | 9/2005 |
| GB | 1433415 | 4/1976 |
| JP | 04500143 | 1/2001 |
| JP | 03180743 | 7/2003 |
| WO | 0051560 | 9/2000 |
| WO | WO 02/83028 | 10/2002 |
| WO | WO 03/051260 | 6/2003 |
| WO | 2005107671 | 11/2005 |

OTHER PUBLICATIONS

Office Action dated Mar. 17, 2011 for corresponding Korean Patent Application No. 10-2009-7006281 (with English summary).
English Translation of Notice of Reasons for Rejection dated Jul. 13, 2001 for Japanese application No. 2009-526686.
Canadian Examination Report dated Nov. 18, 2011 from Canadian Application No. 2,662,116.
Japanese Office Action (English translation) dated Aug. 7, 2012 for Japanese application No. 2009-526686.

\* cited by examiner

*Primary Examiner* — Lynne Anderson

(74) *Attorney, Agent, or Firm* — Ohlandt, Greeley, Ruggiero & Perle, L.L.P.

(57) ABSTRACT

A tampon removal device is provided that has one or more malodor counteractants, perfumes, medicines including analgesics, anti-bacterials, lubricants and/or moisturizers, visual stimulators and/or identifiers including color code, color modification, and optical enhancer, a ply variation, a polymer modification, or a surface modification.

15 Claims, No Drawings

TAMPON REMOVAL DEVICE

CROSS-REFERENCES TO RELATED APPLICATIONS

This application claims the benefit of U.S. Provisional Application Ser. No. 60/840,886, filed on Aug. 29, 2006, the contents of which are incorporated by reference herein.

BACKGROUND OF THE INVENTION

1. Field of the Invention

The present invention relates generally to tampon removal devices. More particularly, the present invention relates to a tampon removal device having one or more attributes besides the ability of a normal tampon removal device. The one or more attributes are achieved by the inclusion in the tampon removal device of one or more of: a malodor counteractant, a perfume, a medicine, a lubricant and/or moisturizer, an antibacterial, a visual stimulator, a ply modification, a polymer modification, or a surface modification.

2. Description of the Related Art

A tampon or tampon pledget has a string for removal of a tampon after use. The string is normally made of a single ply or multiple plies of yarn. Generally, the tampon string is only used by a user to remove the pledget from the body.

There is a need to have a tampon string absorb or indicate when the pledget has absorbed body fluids, such as, menstrual fluid from the vagina.

There is a need for a tampon string that has other properties and therefore benefits to the user.

SUMMARY OF THE INVENTION

The present invention provides a tampon or tampon pledget removal device that has a malodor counteractant for reduction of odor inside and/or outside the body of the user.

The present invention also provides a tampon removal device having a perfume for reduction of odor inside and/or outside the body of the user.

The present invention further provides a tampon removal device having a medicine for administering such medicine inside and outside the body of the user.

The present invention still further provides a tampon removal device having a lubricant and/or moisturizer to facilitate insertion and removal of the tampon pledget into and out of the body of the user.

The present invention yet further provides a tampon removal device having an antibacterial agent for reduction of bacteria inside and outside the body of the user.

The present invention also provides a tampon removal device having a visual stimulation and/or identification, which include color code, color modification, and optical enhancer.

The present invention additionally provides a tampon removal device having a ply modification, a polymer modification, or a surface modification.

These and other objects and advantages of the present invention are achieved by a tampon removal device having one or more of the following: a malodor counteractant, a perfume, a medicine, a lubricant and/or moisturizer, an antibacterial agent, a visual stimulator, a ply, a polymer modification, a surface modification, or any combinations thereof.

The above-described and other features and advantages of the present disclosure will be appreciated and understood by those skilled in the art from the following detailed description.

DETAILED DESCRIPTION OF THE INVENTION

The present invention relates to a tampon or tampon pledget removal device or string. The present tampon removal device has one or more benefits besides the ability to remove the tampon from the user. The benefits are achieved by adding into or applying one or more ingredients to the removal device. Such ingredients can include visual stimulators, such as color codes or color modifications or optical enhancers. Also, such benefits can be achieved by a ply modification, or a polymer modification, or a surface modification to the removal device.

Known tampon removal strings have multiple strands or plies of yarn twisted or woven together. The removal device of the present invention can be any material that could be used to remove a tampon from a body cavity. Such material, includes, but not limited to, natural fiber and yarn, synthetic fiber and yarn, woven tape, knitted tape, extruded tape, coated tape, spun bonded tape, felt, or any combinations thereof. Preferably, the tampon removal device of the present invention has multiple woven, wrapped, spun, knit, crocheted, braided, and/or extruded piles of yarn.

Preferably, the tampon removal device is a material of about 500 denier to about 10000 denier, and more preferably, about 1500 denier to about 3000 denier. Denier is a value equal to weight in grams per 9000 meters. Preferably, the tampon removal device has a length between about 2 inches to about 24 inches, and more preferably, about 4 inches to about 6 inches.

The benefits of the tampon removal devices of the present invention are achieved, in part, by the inclusion of one or more of the following: a malodor counteractant for reduction of odor inside and/or outside the body of the user, a perfume for reduction of odor outside the body of the user, a medicine and/or analgesic inside and outside the body of the user, a lubricant and/or moisturizer to facilitate insertion and removal of the tampon pledget into and/or out of the body of the user, or an antibacterial agent for reduction of bacteria inside and/or outside the body of the user.

The malodor counteractant is an odor abatement material that preferably is an odor adsorber. The malodor counteractant can be any suitable material capable of adsorbing, suppressing, neutralizing, reducing and/or eliminating odors emanating from body fluids, such as, for example, menstrual fluid, urine, perspiration or fecal matter to provide protection against odor outside of the body associated with the body fluids.

A suitable malodor counteractant is one or more zeolites, glycerin compounds, natural oils, solutions of soluble natural compounds, natural plant and herb extracts, naturally occurring deodorizing actives, acids, bases, anti-oxidants, chelating agents, aldehydes, esters, oxidizing agents, biological agents, surfactants, surface active polymers, compositions manufactured and sold under the tradename Shaw Mudge Spring Fresh49630-A manufactured by Shaw Mudge, or any combinations thereof.

The malodor counteractant may be present in an amount about 0.025% by weight (w/w) to about 5.0% w/w based on total weight of the removal device. Preferably, the malodor counteractant is present in an amount about 0.5% w/w to 2.5% w/w based on the total weight of the removal device.

The zeolite for use in the present invention can be in powdered or granular form. Preferably, the zeolite is a natural zeolite.

Suitable glycerin compounds for use in the present invention include, but are not limited to, glycolic acid, glycerin stearate, glycerin monolaurate, glycerin monoalkyl ether, or any combinations thereof.

Suitable aldehydes include, but are not limited to, acyclic aliphatic, non-terpenic aliphatic, non-terpenic alicyclic, terpenic, aliphatic aldehyde substituted by an aromatic group, bifunctional, aldehyde having an unsaturation carried by the carbon in the alpha position of the aldehyde function conjugated with an aromatic ring, aldehyde having the function carried by an aromatic ring, or any combinations thereof.

Natural oils suitable for use in the present tampon removal device include, but are not limited to, white cedar leaf oil, tea tree oil, hypericon oil, rosemary oil, clove oil, ginger oil, turmeric oil, chamomile oil, lemon grass oil, thyme oil, achillea oil, thulasi oil, clary sage oil, cedar (hinoki) oil, or any combinations thereof.

Solutions of a soluble natural compound include, but are not limited to, chlorophyll.

Natural plant and herb extracts suitable for use in the present tampon removal device include, but are not limited to, green tea extract.

Suitable naturally occurring deodorizing actives for use in the present tampon removal device include, but are not limited to, farnesol, phenoxyethanol, alkali rhodanide, linalool, citronellol, geraniol, phenethyl alcohol, or any combinations thereof.

Acids suitable for use in the present invention include, but are not limited to, citric acid, acetic acid, undecylenic acid, esters of undecylenic acid, salt of undecylenic acid, organic acids safe for use in the body, or any combinations thereof.

Suitable bases for use as a malodor counteractant in the present invention include, but are not limited to, ammonia, triethanolamine, or any combinations thereof.

Anti-oxidants suitable for use as a malodor counteractant in the present invention include, but are not limited to, ascorbic acid including iso-ascorbic acid, vitamin E, and any combinations thereof.

Suitable chelating agents for use as a malodor counteractant in the present invention include, but are not limited to, ethylenediaminetetraacetic acid (EDTA), nitrilotriacetic acid (NTA), inorganic salts of these two materials, or any combinations thereof.

Esters suitable for use as a malodor counteractant in the present invention include, but are not limited to, a mixture of geranyl crotonate and dihexyl fumerate.

Suitable oxidizing agents for use as a malodor counteractant in the present invention include, but are not limited to, hydrogen peroxide, sodium hypochlorite, or any combinations thereof.

Biological agents suitable for use as a malodor counteractant in the present invention include, but are not limited to, bacterial spore, enzyme, or any combinations thereof.

Certain surfactants can be used as a malodor counteractant in the present invention to provide malodor counteractant properties. Such malodor counteractant surfactants include, but are not limited to, sodium alkyl ethoxy sulfate, alkyalkoxylated phosphate ester sodium salt, dioctylester of sodium sulfosuccinic acid, dioctyl sulfosuccinate, ammonium salt of polycarboxylic acid, potassium slat of complex organic phosphate ester, ammonium lauryl ether sulfate, polyoxyethylene including polyoxyethylene stearic acid, polyethylene 20, polyoxyethylene 40 hydrogenated castor oil, polyoxyethylene sorbitan monostearate and polyoxyethylene 20 sorbitan monostearate, alkanolamides, isostearyl alcohol, polyoxyethylene/polyoxypropylene block copolymer, glycerol mono/dioleate, glycol distearate, ethoxylated linear alcohols (50% ethoxylated), PEG-2 stearate, polyoxyalkylated isostearyl alcohol, triglycerol monooleate, polysorbate 80, glycerol monostearate, diglyceryl diisostearate, silicone glycol copolymer, polyglyceryl ester, ethoxylated alcohol, glycol ester, trimethyl coco quaternary ammonium chloride, distearyl dimonium chloride, benzalkonium chloride, benzethonium chloride, coconut-based imidazoline or dicarboxylate or sodium slat, coco amido betaine, betaine derivative, octyl diporpionate, cocamphoglycinate, cetyl dimethicone copolyol, dialkoxy dimethyl polysiloxane, polysiloxane polyakyl copolymer, or any combinations thereof.

Surface active polymers suitable for use as a malodor counteractant in the present invention include, but are not limited to, acrylate/C10-30 alkyl acrylate crosspolymer.

The perfume for use in the tampon removal device of the present invention reduces odor associated with body fluids and deodorizes outside the body of the user. The perfume is a scent. The perfume may be any deodorant, powder, or a fragrance that can be inserted into the body. Examples of perfumes suitable for use in the present tampon removal device include, but are not limited to, compositions manufactured and sold under the tradename Givaudan Floral Rose 2438-23-01, compositions manufactured and sold under the tradename Givaudan PCC-10700, or any combinations thereof. The amount of perfume material may be about 0.025% w/w to about 5.0% w/w by weight on the removal device.

A medicine as used herein is defined as including analgesics, and may be provided in the tampon removal device. Health administering formulations may be delivered inside and outside the body via the impartation of medicine into the tampon removal device. Thus, treating, prohibiting, reducing the harmful effects, and/or curing ailments afflicting the user may be achieved by the tampon removal device. Such medicines that are suitable for use in the tampon removal device of the present invention include, but are not limited to, acetylsalicylic acid (aspirin), ibuprofen, other non-steroidal anti-inflammatory drugs (NSAID's), botanical extract, botanical active, St. John's Wort, soluble wheat protein, spirulina, ginseng, milk thistle, glucosamine, witch hazel, green tea extract, chamomile, or any combinations thereof. NSAIDs are used to relieve some symptoms caused by arthritis (rheumatism), such as inflammation, swelling, stiffness, and joint pain. Some NSAIDs are also used to relieve other kinds of pain or to treat other painful conditions, such as, gout attacks, bursitis, tendinitis, sprains, strains, or other injuries, or menstrual cramps. NSAIDs, such as, Ibuprofen and naproxen, are also used to reduce fever. The amount of medicine may be about 0.025% w/w to about 5.0% w/w or based on the total weight of the tampon removal device.

Lubricants and/or moisturizers may be imparted into the tampon removal device of the present invention. Lubricants and/or moisturizers increase the smoothness and suppleness of the skin, prevent or relieve dryness of the skin, and/or protect the skin. The impartation of lubricants or moisturizers into the tampon removal device allows the tampon removal device to administer the lubricant or moisturizer inside and outside of the user's body. Such lubricants and/or moisturizers suitable for use in the tampon removal device of the present invention includes, but is not limited to, petrolatum, stearic acid, emollient, stearyl alcohol, stearic fatty acid, isoparaffin, triglyceride, magnesium stearate, erucamide, oleamide, stearamide, zinc stearate, epoxidized soybean oil, wax, silicon, or any combinations thereof. The amount of lubricant may be about 0.025% w/w to 5.0% w/w by total weight on the removal device.

The tampon removal device may be provided with an antibacterial agent. The anti-bacterial agent is effective to reduce or inhibit the growth of bacteria such as, for example, *S. aureus* bacteria. Such anti-bacterial agents suitable for use in the tampon removal device of the present invention include, but are not limited to, povidone-iodine compound, zinc, silver, penicillin, erythromycin, vancomycin, nitrofurazone, benzethonium chloride, or any combination thereof. Thus, the incorporation of an anti-bacterial agent into the tampon removal device reduces bacteria inside and outside of the user's body. The amount of anti-bacterial may be about 0.025% w/w to 3.0% w/w by total weight on the removal device.

The tampon removal device may be imparted with a visual stimulator. The visual stimulator is imparted onto the tampon removal device to provide product identification color codes, visual identifiers, color modifications, optical enhancers, or any combinations thereof. The visual stimulators or product identification color codes, visual identifiers, color modifications, optical enhancers may include, for example, one or more dyes, pigments, colorants, additives, or physical/mechanical designs and techniques. The visual stimulators indicate to a user that the tampon or tampon removal device includes any of the additional materials described above or other tampon or tampon removal device properties or benefits. Thus, improved visual stimulation assists users in identifying tampon types and product characteristics via the removal device modifications and improvements that are provided.

The tampon removal device may be modified with materials and processes to improve wearing comfort characteristics and gripability. The modifications are, for example, a ply modification; a polymer modification, such as a polymer blend or copolymer blend modification, a finish, such as a wax; a surface modification, such as a texture modification, or any combinations thereof. In addition, the modifications improve wearing comfort characteristics and grip ability to provide an improved ability to identify tampon sorts and product characteristics over the prior art.

The following methods may be used to add one or more ingredients, such as a malodor counteractant, a perfume, a medicine and/or analgesic, a lubricant and/or moisturizer, an antibacterial agent, into and/or outside the removal device or, provide visual stimulators, such as color codes or color modifications or optical enhancers into and/or outside the removal device. Thus, these one or more ingredients may be added on a surface and/or within the material of the removal device.

The combination of the one or more ingredients and/or the visual stimulators (the "additional material") on and perhaps into the tampon removal device can be achieved by a kiss roll application. The kiss roll application provides removal device material through a feeder. The removal device material is thread through directors from the feeder. The directors may be, for example, tubing or loops. The removal device material extends from the directors onto a metering roll. The metering roll has the additional material applied on an outer surface. Upon contact, the additional material is transferred from the outer surface of the metering roll to the tampon removal device material. The metering roll may continuously apply the additional material by rotating into a container, preferably positioned remote from the tampon removal device material, holding a liquid material such as, for example, the malodor counteractant, and rotating out of the container into contact with the tampon removal device material. The tampon removal device material extends from the metering roll to a spool or package take-up. The tampon removal device material is wound about the package take-up. The metering roll, preferably, rotates in the direction of the movement of the removal device material. The tampon removal device material is substantially taut between the feeder and the package take-up. The rotation of the metering roll and/or the package take-up may move or assist in moving the removal device material from the feeder to the package take-up.

The combination of the one or more ingredients and/or visual stimulators on and perhaps into the tampon removal device can, alternatively, be achieved by a metering application. The metering application provides removal device material through a feeder. The tampon removal device material is thread around or through removal device directors from the feeder. The directors may be, for example, tubing, loops or knobs. The tampon removal device material is thread through a metering applicator that injects the additional material such as, for example, the malodor counteractant, onto the removal device material. The metering applicator has a pump to transfer the additional material from a holding container to the applicator and onto the removal device material. The tampon removal device material extends from the metering roll to a spool or package take-up. The tampon removal device material is wound about the package take-up. The tampon removal device material is substantially taut between the feeder and the package take-up. The rotation of the package take-up may move or assist in moving the removal device material from the feeder to the package take-up.

The combination of the one or more ingredients and/or visual stimulators in the tampon removal device can be achieved, in another alternative, by an exhaust application. Packages of tampon removal devices are placed into a dye kettle, preferably, about tubing having a plurality of apertures. The additional ingredient such as, for example, the malodor counteractant, is pumped through the packages of tampon removal device. Preferably, a remote pump and holding container pumps the additional material through the tubing out of the plurality of apertures onto the packages of removal device. The additional material is exhausted into the removal device. The tampon removal device packages are post dried and cured to form the finalized individual tampon removal device.

Alternatively, the combination of the one or more ingredients and/or visual stimulators ("the additional material") on or into the tampon removal device may be produced by roller coating, saturation, kiss coating, spray coating, metering technique, dye bath technique, powder coating, heat treatment, cure treatment, space dying technique, or any combinations thereof.

Example 1

In one embodiment according to the present invention, the malodor counteractant (the "additional material") is an undecylenic acid, such as, for example, malodor counteractant compositions containing odor neutralizing agents provided in U.S. Pat. No. 6,495,097 which is incorporated by reference herein in its entirety. The malodor counteractant compositions containing odor neutralizing agents may include undecylenic acid. The undecylenic acid and/or its derivative may be contained in a fragranced or, preferably, an unfragranced carrier. Preferably, the tampon removal device has a malodor counteractant for reducing malsensory agents while allowing release of a selected component including undecylenic acid or a derivative thereof with the undecylenic acid or the derivative being in an amount effective to reduce the malsensory agent and allow release of the component from the composition, and where the derivative of undecylenic acid further includes a ratio of methyl ester to ethyl ester in a range of approximately 5/95 to approximately 30/70.

Applicants conducted testing of tampon strings having a malodor counteractant sold commercially by Shaw Mudge and Company under the tradename OdorSynthesis® II. The malodor counteractant is for reducing malsensory agents that allowed release of a selected component including undecylenic acid or a derivative thereof with the undecylenic acid and the derivative being in an amount effective to reduce the malsensory agent and allow release of the component from the composition. The derivative of undecylenic acid further includes a ratio of methyl ester to ethyl ester in a range of approximately 5/95 to approximately 30/70.

Solid Phase Microextraction (SPME) technique and gas chromatography/mass spectroscopy (GC/MS) instruments were used to prepare and analyze samples. SPME uses a fiber, for example, coated with a liquid (polymer), a solid (sorbent), or a combination of both. The fiber coating removes the compounds from the sample, for example, in a headspace above a solid or liquid material, by absorption in the case of liquid coatings or adsorption in the case of solid coatings. The SPME fiber is then inserted directly into the gas chromatograph (GC). Once extracted from the substrate or coating, the sample identification of that extract is done using GC/MS. The GC not only separates the components of the headspace mix based roughly on relative volatility or boiling point, but also includes a "mass-selective" detector. The detector or mass spectroscopy functions by using energy to take apart the molecule that elutes from the chromatograph into components to form "daughter" molecular ions. A computer is used to analyze the data, checking to see if the pattern matches that of a database of compounds to see what the compound's "parent" structure really is. Since so few compounds have the same boiling point and the same molecular ion profile, SPME can be used to extract the material into the headspace, then headspace GC/MS can be used to get very clear identifications for even complex, large molecules. Tables 1a through 1d provide parameters for the malodor, analytical method, sampling method, and sample preparation for the testing results shown in Tables 2 and 3.

Table 1a provides a combination of malodors used for the testing results shown in Tables 2 and 3. The combination included five components, three combined for the feminine or menstrual malodor, one fecal malodor, and one urine malodor. The feminine malodor included trimethylamine, iso valeric acid, and putrescline. The fecal malodor was skatole. The urine malodor was ammonia.

Table 1b provides parameters of the analytical method using SPME Headspace and GC/MS for the testing results shown in Tables 2 and 3. The analytical method used a gas chromatograph, detector or mass spectroscopy, and a SPME fiber. The gas chromatograph included an oven, a front inlet, a front detector, and a column.

Table 1c provides a sampling method for the testing results shown in Tables 2 and 3. This sampling method was used for SPME headspace analysis.

Table 1d provides parameters for sample preparation for the testing results shown in Tables 2 and 3. Samples were prepared for the malodor, tampon strings, and headspace vials.

The Sample column of Table 2 includes a wet process string lot that includes removal devices that each have 1% w/w by weight of the malodor counteractant applied thereto. Each of the wet processed string lot had the malodor counteractant applied by an exhaust application described above. At this time, it is believed the exhaust application is the preferred method of applying the malodor counteractant. Each of the wet processed removal devices of the wet processed string lot had an anti-wicking material applied thereto. Preferably, anti-wicking material is applied by exhaust application as described above. Malodor counteractant and anti-wicking material that are applied by the same method may provide economical and efficiency advantages. The control removal device lot included cotton removal devices that had been bleached and had an anti-wicking material applied thereto. The control removal device lot had malodor applied thereon and was free of malodor counteractants. The malodor control included the malodor in a vial. The malodors included a combination of five components, three combined for the feminine or menstrual malodor, one fecal malodor, and one urine malodor. The feminine malodor included trimethylamine, iso valeric acid, and putrescline. The fecal malodor was skatole. The urine malodor was ammonia. Strings having the malodor thereon included all five components. The GC separated the components of the headspace mix for analysis, as shown in Table 2. The malodor peak area is an area under a curve generated and analyzed with head space samples injected into a GC/MS. The % reduction compares a malodor peak area of the control string lot or wet process string lot to a malodor peak area of the malodor control.

Table 3 includes testing of removal devices that have 1% w/w to 5% w/w by weight of the malodor counteractant. Removal devices that have 1% w/w of the malodor counteractant are indicated by "421-5". Removal devices that have 3% w/w of the malodor counteractant are indicated by "421-1". Removal devices that have 5% w/w of the malodor counteractant are indicated by "421-3". Antiwicking material was applied to the removal devices by exhaust treatment to the yarn included therein. The malodor counteractant was subsequently applied to the removal devices by a metering application described herein. The control removal device lot was a cotton removal device that had been bleached and had an antiwicking material applied thereto. The control removal devices had malodor applied thereon and was free of malodor counteractants. Removal devices were either heated or non-heated. The "not heated" removal devices and control removal devices were not heated. The "heated" removal devices were heated at low temperature, for example, 100° F. to 250° F. for, preferably, about 1 hour. The malodors included a combination of five components, three combined for the feminine or menstrual malodor, one fecal malodor, and one urine malodor. The feminine malodor included trimethylamine, iso valeric acid, and putrescline. The fecal malodor was skatole. The urine malodor was ammonia. Strings having the malodor thereon included all five components. The GC separated the components of the headspace mix for analysis, as shown in Table 3. The malodor peak area is the area under a curve generated and analyzed with head space samples injected into a GC/MS. The % reduction compares a malodor peak area of the control string to a malodor peak area of the "not heated" or "heated" removal device.

TABLE 1a

| MALODOR: | 1. Feminine Malodor including trimethylamine, isovaleric acid, and putrescine |
|---|---|
| | 2. skatole |
| | 3. ammonia ($NH_3$) |

TABLE 1b

ANALYTICAL METHOD: SPME Headspace/GC/MS
METHOD PARAMETERS JESPME4

GC

| | | |
|---|---|---|
| Oven | Initial Temperature: | 55° C. |
| | Ramp Rate: | 25.0° C./minute |
| | Final Temperature: | 260° C. |
| | Run time: | 9.90 minutes |
| Front Inlet | Mode: | Splitless |
| | Initial Temperature: | 240° C. |
| | Pressure: | 24.90 pounds per square inch (psi) |
| | Total Flow | 505.10 milliliters/minute (mL/min.) |
| Front Detector | Temperature: | 250° C. |
| | Flow: | 40 mL/min. |
| | Mode: | Constant Pressure |
| | Makeup gas type: | Helium |
| Column | Type: | Capillary |
| | Model: | Sold commercially under the tradename Phenomenex ® Zebron DB-1 |
| | Specs: | 0.25 millimeters (mm)/60 meters (m)/0.25 micrometers(μm) |

Mass Spectroscopy

| | | |
|---|---|---|
| SCAN Parameters (Molecular Weight Ranges) | Low Mass: | 35.00 atomic mass unit (amu) |
| | High Mass: | 455.00 amu |
| | Threshold: | 140 amu |

SPME

| | | |
|---|---|---|
| SPME Fiber | TYPE: | 100 μm polydimethylsiloxane (PDMS) |
| | Linear Range: | 10 parts per billion (ppb)/1 ppm |
| | Molecular range: | 30-300 amu |

TABLE 1c

| | |
|---|---|
| SAMPLING METHOD: | 20 mL Headspace vials at 10 minutes equilibration |

TABLE 1d

SAMPLE PREPARATION:

1. Prepared solutions of the following:
   1. Feminine Malodor including trimethylamine, iso valeric acid, and putrescine
   2. skatole (1%)
   3. ammonia (1000 ppm) standard
2. 0.02 grams malodor solution deposited onto tampon string in 20 mL headspace vial
3. Headspace vial sealed and analyzed by SPME headspace

TABLE 2

| SAMPLE | MALODOR | MALODOR PEAK AREA | REDUCTION OF MALODOR |
|---|---|---|---|
| Malodor Control | Trimethylamine | 251.05 | |
| Control String Lot | Trimethylamine | 250.97 | 0.04% |
| Wet Process String Lot | Trimethylamine | 20.32 | 91.91% |
| Malodor Control | iso valeric acid | 105.31 | |
| Control String Lot | iso valeric acid | 105.27 | 0.04% |
| Wet Process String Lot | iso valeric acid | 9.89 | 90.61% |
| Malodor Control | Putrescine | 75.77 | |
| Control String Lot | Putrescine | 75.74 | 0.04% |
| Wet Process String Lot | Putrescine | 6.57 | 91.33% |
| Malodor Control | Skatole | 324.75 | |
| Control String Lot | Skatole | 324.71 | 0.02% |
| Wet Process String Lot | Skatole | 19.28 | 94.07% |
| Malodor Control | Ammonia | 55.48 | |
| Control String Lot | Ammonia | 55.46 | 0.04% |
| Wet Process String Lot | Ammonia | 4.86 | 91.25% |

TABLE 3

| SAMPLE | MALODOR | MALODOR PEAK AREA | REDUCTION OF MALODOR |
|---|---|---|---|
| Control String | Trimethylamine | 250.99 | |
| 421-1 not heated | Trimethylamine | 21.22 | 91.55% |
| 421-1 heated | Trimethylamine | 21.25 | 91.54% |
| Control String | iso valeric acid | 105.25 | |
| 421-1 not heated | iso valeric acid | 10.06 | 90.45% |
| 421-1 heated | iso valeric acid | 10.07 | 90.44% |
| Control String | Putrescine | 75.75 | |
| 421-1 not heated | Putrescine | 7.05 | 90.71% |
| 421-1 heated | Putrescine | 7.05 | 90.71% |
| Control String | Skatole | 324.71 | |
| 421-1 not heated | Skatole | 20.87 | 93.58% |
| 421-1 heated | Skatole | 20.86 | 93.58% |
| Control String | Ammonia | 55.45 | |
| 421-1 not heated | Ammonia | 5.22 | 90.61% |
| 421-1 heated | Ammonia | 5.23 | 90.59% |
| Control String | Trimethylamine | 250.99 | |
| 421-3 not heated | Trimethylamine | 19.52 | 92.23% |
| 421-3 heated | Trimethylamine | 19.52 | 92.23% |
| Control String | iso valeric acid | 105.28 | |
| 421-3 not heated | iso valeric acid | 8.36 | 92.07% |
| 421-3 heated | iso valeric acid | 8.37 | 92.06% |
| Control String | Putrescine | 75.75 | |
| 421-3 not heated | Putrescine | 5.11 | 92.26% |
| 421-3 heated | Putrescine | 5.11 | 92.26% |
| Control String | Skatole | 324.71 | |
| 421-3 not heated | Skatole | 16.71 | 94.86% |
| 421-3 heated | Skatole | 16.72 | 94.86% |

TABLE 3-continued

| SAMPLE | MALODOR | MALODOR PEAK AREA | REDUCTION OF MALODOR |
|---|---|---|---|
| Control String | Ammonia | 55.45 | |
| 421-3 not heated | Ammonia | 3.84 | 93.08% |
| 421-3 heated | Ammonia | 3.84 | 93.08% |
| Control String | Trimethylamine | 250.99 | |
| 421-5 not heated | Trimethylamine | 16.24 | 93.54% |
| 421-5 heated | Trimethylamine | 16.24 | 93.54% |
| Control String | iso valeric acid | 105.28 | |
| 421-5 not heated | iso valeric acid | 7.05 | 93.31% |
| 421-5 heated | iso valeric acid | 7.05 | 93.31% |
| Control String | Putrescine | 75.75 | |
| 421-5 not heated | Putrescine | 3.98 | 94.75% |
| 421-5 heated | Putrescine | 3.98 | 94.75% |
| Control String | Skatole | 324.71 | |
| 421-5 not heated | Skatole | 15.12 | 95.35% |
| 421-5 heated | Skatole | 15.12 | 95.35% |
| Control String | Ammonia | 55.45 | |
| 421-5 not heated | Ammonia | 3.01 | 94.58% |
| 421-5 heated | Ammonia | 3.01 | 94.58% |

The results shown in Tables 2 and 3 provide that tampon strings that include between about 1% w/w to about 5% w/w by weight of the malodor counteractant having a derivative of undecylenic acid that includes a ratio of methyl ester to ethyl ester in a range of approximately 5/95 to approximately 30/70 reduces odors. Such odors were created by trimethylamine, iso valeric acid, putrescine, skatole, and ammonia; and reductions were at least 90.44%, as compared to a control string without a malodor counteractant. In addition, heating the string having the malodor counteractant thereon has little or no effect on reducing odors created by trimethylamine, iso valeric acid, putrescine, skatole, and ammonia. Thus, the malodor counteractant that includes a ratio of methyl ester to ethyl ester in a range of approximately 5/95 to approximately 30/70 may reduce and/or eliminate odors emanating from body fluids, such as, for example, menstrual fluid, urine, perspiration or fecal matter to provide protection against odor outside of the body associated with the body fluids.

While the present invention has been described with reference to one or more exemplary embodiments, it will be understood by those skilled in the art that various changes may be made and equivalents may be substituted for elements thereof without departing from the scope thereof. In addition, many modifications may be made to adapt a particular situation or material to the teachings of the present invention without departing from the scope thereof. Therefore, it is intended that the present invention be not be limited to the particular embodiment(s) disclosed as the best mode contemplated for carrying out this invention.

What is claimed is:

1. A string for a tampon pledget comprising: a string body made of a material selected from the group consisting of natural fiber, synthetic fiber, woven tape, extruded tape, coated tape, spun bonded tape, felt, and any combinations thereof, wherein the string body provides for removal of the tampon pledget from a body cavity, the string body having a malodor counteractant, wherein said malodor counteractant is present in an amount of 1.0% by weight to 5.0% by weight based on a total weight of said string body, wherein said malodor counteractant is within said material of said string body, and wherein said malodor counteractant is for reduction of odor inside and outside a body of a user.

2. The string of claim 1, wherein said malodor counteractant is selected from the group consisting of one or more zeolites, glycerin compounds, natural oils, solutions of soluble natural compounds, natural plant and herb extracts, naturally occurring deodorizing actives, acids, bases, antioxidants, chelating agents, aldehydes, esters, oxidizing agents, biological agents, surfactants, surface active polymers, and any combinations thereof.

3. The string of claim 1, wherein said malodor counteractant has a derivative of undecylenic acid that includes a ratio of methyl ester to ethyl ester in a range of about 5/95 to about 30/70.

4. The string of claim 3, wherein the string has about 1% by weight based on a total weight of said string body of said malodor counteractant.

5. The string of claim 1, wherein said string body has said malodor counteractant applied through said material by an exhaust application.

6. The string of claim 1, further comprising a second modification incorporated in the string body that is a perfume for reduction of odor outside the body of the user.

7. The string of claim 6, wherein said perfume is selected from the group consisting of a deodorant, a powder, and a fragrance.

8. The string of claim 1, further comprising a second modification incorporated in the string body that is a medicine for treating, prohibiting, reducing harmful effects, and/or curing ailments afflicting the user.

9. The string of claim 8, wherein said medicine is selected from the group consisting of acetylsalicylic acid, ibuprofen, other non-steroidal anti-inflammatory drugs, botanical extract, botanical active, St. John's Wort, soluble wheat protein, spirulina, ginseng, milk thistle, glucosamine, witch hazel, green tea extract, chamomile, and any combinations thereof.

10. The string of claim 1, further comprising a second modification incorporated in the string body that is a lubricant and/or moisturizer to facilitate insertion and removal of the tampon pledget into and/or out of the body of the user.

11. The string of claim 10, wherein said lubricant and/or moisturizer is petrolatum, stearic acid, emollient, stearyl alcohol, stearic fatty acid, iso-paraffin, triglyceride, magnesium stearate, erucamide, oleamide, stearamide, zinc stearate, epoxidized soybean oil, wax, silicon, and any combinations thereof.

12. The string of claim 1, wherein the string body has one of a plurality of visual stimulators throughout the string body that provides an identification color code to assist users in identifying product characteristics via the string body, and wherein said plurality of visual stimulators identifies at least two characteristics selected from the group consisting of a malodor counteractant, a perfume, a medicine, a lubricant, a moisturizer, and any combinations thereof.

13. A plurality of strings each for a tampon pledget comprising: a plurality of string bodies each made of a material, wherein each of the plurality of string bodies provides for removal of the tampon pledget from a body cavity, each of the plurality of string bodies having one of a plurality of visual stimulators throughout each of said plurality of string bodies that provides an identification color code to assist users in identifying product characteristics via the plurality of string bodies, said plurality of visual stimulators identifying at least two characteristics selected from the group consisting of a malodor counteractant, a perfume, a medicine, a lubricant, a moisturizer, and any combinations thereof.

14. The plurality of strings of claim 13, wherein each of the plurality of string bodies is selected from the group consisting of natural fiber, synthetic fiber, woven tape, extruded tape, coated tape, spun bonded tape, felt, and any combinations thereof.

15. The string of claim 13, wherein each of said visual stimulators comprises a visual material selected from the group consisting of dye, pigment, colorant, additive, and any combination thereof.

* * * * *